US008873716B2

(12) United States Patent
Ren et al.

(10) Patent No.: US 8,873,716 B2
(45) Date of Patent: *Oct. 28, 2014

(54) METHOD AND SYSTEM FOR CONTROLLING X-RAY FOCAL SPOT CHARACTERISTICS FOR TOMOSYNTHESIS AND MAMMOGRAPHY IMAGING

(71) Applicant: Hologic, Inc., Bedford, MA (US)

(72) Inventors: Baorui Ren, Andover, MA (US); Jay Stein, Boston, MA (US); Zhenxue Jing, Chadds Ford, PA (US); Andrew Smith, Lexington, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/905,264

(22) Filed: May 30, 2013

(65) Prior Publication Data

US 2013/0259192 A1 Oct. 3, 2013

Related U.S. Application Data

(62) Division of application No. 12/623,472, filed on Nov. 23, 2009, now Pat. No. 8,457,282.

(60) Provisional application No. 61/117,453, filed on Nov. 24, 2008.

(51) Int. Cl.
| | |
|---|---|
| G21K 1/08 | (2006.01) |
| H01J 35/30 | (2006.01) |
| G01N 23/083 | (2006.01) |
| A61B 6/02 | (2006.01) |
| H05G 1/52 | (2006.01) |
| H01J 35/14 | (2006.01) |
| A61B 6/00 | (2006.01) |
| A61B 6/03 | (2006.01) |

(52) U.S. Cl.
CPC .............. *A61B 6/4021* (2013.01); *H05G 1/52* (2013.01); *H01J 35/14* (2013.01); *A61B 6/502* (2013.01); *A61B 6/025* (2013.01); *A61B 6/032* (2013.01)
USPC ................ 378/137; 378/27; 378/37; 378/145

(58) Field of Classification Search
USPC .......... 378/4, 12, 21, 22, 27, 37, 91, 93, 98.6, 378/125, 126, 135–137, 145, 146, 204, 205, 378/210
See application file for complete search history.

(56) References Cited

U.S. PATENT DOCUMENTS

| | | | |
|---|---|---|---|
| 5,274,690 | A | 12/1993 | Burke |
| 5,313,510 | A | 5/1994 | Ebersberger |

(Continued)

FOREIGN PATENT DOCUMENTS

| | | |
|---|---|---|
| EP | 1028451 | 8/2000 |
| WO | WO9803115 | 1/1998 |

(Continued)

OTHER PUBLICATIONS

International Search Report and Written Opinion from related PCT application PCT/US09/065451 dated Feb. 5, 2010.

(Continued)

*Primary Examiner* — Anastasia Midkiff (57) ABSTRACT

An x-ray tube is described that includes components for increasing x-ray image clarity in the presence of a moving x-ray source by modifying focal spot characteristics, including focal spot size and focal spot position. In a first arrangement a static focal spot is moved in a direction contrary to the movement of the x-ray source so that an effective focal spot position is essentially fixed in space relative to one of the imaged object and/or detector during a tomosynthesis exposure. In a second arrangement, the size of the static focal spot is increased, and the resulting increase in tube current reduces the exposure time and concomitant blur effect. The methods may be used alone or in combination; for example an x-ray tube with a larger, moveable static focal spot will result in a system that fully utilizes the x-ray tube generator, provides a high quality image with reduced blur and, due to the decrease in exposure time, may scan the patient more quickly.

17 Claims, 9 Drawing Sheets

(56) References Cited

U.S. PATENT DOCUMENTS

| | | | |
|---|---|---|---|
| 5,528,658 A | 6/1996 | Hell | |
| 5,841,829 A | 11/1998 | Dolazza | |
| 5,872,828 A | 2/1999 | Niklason | |
| 6,256,369 B1 | 7/2001 | Lai | |
| 6,542,575 B1 | 4/2003 | Schubert | |
| 6,553,096 B1 * | 4/2003 | Zhou et al. | 378/122 |
| 6,895,076 B2 | 5/2005 | Halsmer | |
| 6,940,943 B2 | 9/2005 | Claus | |
| 6,950,492 B2 | 9/2005 | Besson | |
| 6,950,493 B2 | 9/2005 | Besson | |
| 7,001,071 B2 | 2/2006 | Deuringer | |
| 7,016,461 B2 | 3/2006 | Rotondo | |
| 7,110,490 B2 * | 9/2006 | Eberhard et al. | 378/23 |
| 7,116,749 B2 * | 10/2006 | Besson | 378/16 |
| 7,190,758 B2 | 3/2007 | Hagiwara | |
| 7,244,063 B2 | 7/2007 | Eberhard | |
| 7,286,645 B2 | 10/2007 | Freudenberger | |
| 7,319,736 B2 | 1/2008 | Rotondo | |
| 7,356,113 B2 | 4/2008 | Wu | |
| 7,616,731 B2 | 11/2009 | Pack | |
| 7,839,979 B2 | 11/2010 | Hauttmann | |
| 7,885,384 B2 | 2/2011 | Mannar | |
| 8,031,834 B2 | 10/2011 | Ludwig | |
| 8,457,282 B2 * | 6/2013 | Baorui et al. | 378/137 |
| 2002/0126798 A1 | 9/2002 | Harris | |
| 2003/0058989 A1 | 3/2003 | Rotondo | |
| 2004/0109529 A1 | 6/2004 | Eberhard | |
| 2004/0190682 A1 | 9/2004 | Deuringer | |
| 2004/0247081 A1 | 12/2004 | Halsmer | |
| 2004/0264627 A1 | 12/2004 | Besson | |
| 2005/0025278 A1 | 2/2005 | Hagiwara | |
| 2005/0113681 A1 * | 5/2005 | DeFreitas et al. | 600/426 |
| 2005/0133706 A1 | 6/2005 | Eberhard | |
| 2006/0034426 A1 | 2/2006 | Freudenberger | |
| 2006/0126780 A1 | 6/2006 | Rotondo | |
| 2008/0056436 A1 | 3/2008 | Pack | |
| 2008/0285712 A1 * | 11/2008 | Kopans et al. | 378/26 |
| 2010/0020937 A1 | 1/2010 | Hautmann | |
| 2010/0020938 A1 | 1/2010 | Koch | |
| 2010/0189227 A1 | 7/2010 | Mannar | |
| 2010/0303202 A1 | 12/2010 | Ren | |
| 2011/0026667 A1 | 2/2011 | Poorter | |
| 2011/0188624 A1 | 8/2011 | Ren | |
| 2012/0033868 A1 | 2/2012 | Ren | |

FOREIGN PATENT DOCUMENTS

| | | | |
|---|---|---|---|
| WO | WO 2006055830 A2 * | 5/2006 | G06K 9/00 |
| WO | WO2007129244 | 11/2007 | |
| WO | WO2008072144 A1 | 6/2008 | |
| WO | WO2009122328 A1 | 10/2009 | |
| WO | WO2009136349 | 11/2009 | |

OTHER PUBLICATIONS

Kachelriess, 2004 IEEE Nuclear Science Symposium Conference Record, Oct. 16-22, 2004, Rome Italy, vol. 6, pp. 3759-3763.

* cited by examiner

METHOD AND SYSTEM FOR CONTROLLING X-RAY FOCAL SPOT CHARACTERISTICS FOR TOMOSYNTHESIS AND MAMMOGRAPHY IMAGING

This application is a divisional application of pending U.S. application Ser. No. 12/623,472, filed Nov. 23, 2009, which is a non-provisional of U.S. Application Ser. No. 61/117,453, now expired, all of which are hereby incorporated herein by reference in their entireties.

Breast tomosynthesis is a three-dimensional imaging technology that involves acquiring images of a stationary compressed breast at multiple angles during a short scan. The individual images are then reconstructed into a series of thin high-resolution slices that can be displayed individually or in a dynamic cine mode.

Reconstructed tomosynthesis slices reduce or eliminate the problems caused by tissue overlap and structure noise in single slice two-dimensional mammography imaging. Digital breast tomosynthesis also offers the possibility of reduced breast compression, improved diagnostic and screening accuracy, fewer recalls, and 3D lesion localization.

Digital tomosynthesis combines digital image capture and processing with simple tube/detector motion as used in computed tomography (CT), however over a smaller rotational angle than that used in CT. Breast tomosynthesis systems are similar to mammography systems, with a distinct difference being that the x-ray source is moved to a variety of different imaging positions during tomosynthesis image acquisition.

In the interest of efficiency and image quality it is undesirable to stop the x-ray source at each imaging location, since such stop-and-start scanning procedures have been shown to reduce image quality. Many tomosynthesis systems are arranged to smoothly traverse a path during an image scan. As the x-ray source moves into each of several imaging locations in the imaging path, the x-ray source is activated for a short exposure time (in the range of 10 ms-100 ms) and exposure is repeated with a cycle period of 200 ms to 2 seconds. After each exposure the x-ray source is deactivated. As the x-ray source continues its movement toward the next imaging location, the contents of the digital image detector are read out and stored. There is a minimum time period associated with reading the image from the digital detector, and the overall speed of the tomosynthesis scan is determined by the minimum time period for detector read, the exposure time at each location and the number of exposures.

In a conventional x-ray tube the focal spot is static relative to the tube, and since during each exposure period the x-ray source is continuously moved through space the focal spot is moving as well. The resultant focal spot movement causes image blurring and reduces diagnostic accuracy. It would be desirable to identify a mechanism for reducing undesirable image artifacts that result from x-ray source movement during a tomosynthesis or other image scan.

SUMMARY OF THE INVENTION

According to one aspect of the invention, an improved x-ray tube is provided with the capability of modifying a focal spot characteristic to improve image clarity in a tomosynthesis system. The focal spot characteristics are modified by a combination of one or more approaches which include moving the static focal spot during a tomosynthesis exposure and/or changing a size of the static focal spot for tomosynthesis exposures. In one embodiment, a focal spot is moved during a tomosynthesis exposure period in a direction which opposes a directional movement of the x-ray tube through space such that an effective focal spot remains in substantially the same position during the entire tomosynthesis exposure. Such focal spot movement may be achieved by altering a position of a target on an anode or other methods. With such an arrangement a blurring of tomosynthesis images is reduced.

According to another embodiment, focal spot size may be varied in accordance with a type of imaging that is performed, such that a different focal spot size is used to obtain a mammogram or a tomosynthesis image. Alternatively a different focal spot size may be selected based on breast density. Focal spot size may be varied in accordance with an exposure period, with larger focal spots in general having smaller exposure periods. The ability to use a larger focal spot during tomosynthesis images, with a reduced exposure, allows the tomosynthesis scan speed to be increased while fully utilizing the x-ray tube capabilities. The ability to vary focal spot size enables full utilization of x-ray tube capabilities without sacrificing image quality for different imaging modes.

DETAILED DESCRIPTION

Figure 1:
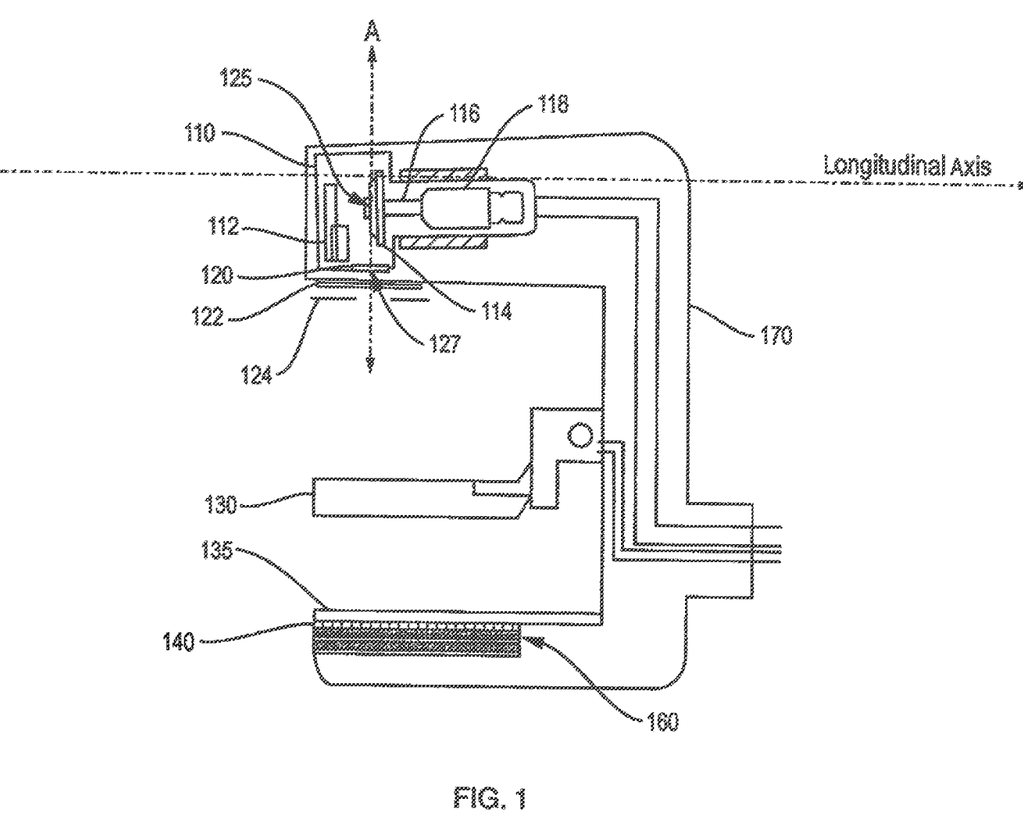
FIG. 1 illustrates a breast tomosynthesis system 100 which includes an x-ray tube of the present invention.

FIG. 1 illustrates a tomosynthesis system 100 which includes an x-ray tube 110, upper and lower compression paddles 130, 135, an anti-scatter grid 140 and a detector 160. The x-ray tube 110 includes a cathode 112, an anode 114 that is mounted on a shaft 116 and rotated by a motor 118, a tube port 120. Also shown attached to the x-ray tube are a filter 122 and a collimator 124.

The x-ray tube is a glass vacuum tube. Within the cathode 112 is a heated filament. When the x-ray tube is turned on, a current is passed through the filament, heating the filament and causing high energy electrons to be dislodged from the filament. A high voltage between cathode and anode causes the electrons to accelerate toward a target location 125 on the anode. The anode is made for example from tungsten and is rotated by motor 118 to avoid local overheating of the target location 125 on the anode.

Electrons are focused to a specific target location by means of a focusing cup (not shown). The focusing cup is a separate control electrode that is cylindrical in shape and that is attached to the cathode, partially surrounding a filament of the cathode.

The dislodged electrons collide with the tungsten atoms of the anode, and x-ray photons are generated having bremsstrahlung radiation and characteristic line emission spectra. X-ray photons are emitted in all directions from the target location 125. The x-ray photons which come out of the tube port 120 are used for imaging. For the purposes of this application, the x-ray photons which come out of the tube port define the static focal spot 127. The static focal spot size refers to the focal spot size at any given instantaneous time moment, as compared to the time-averaged focal spot size during an x-ray exposure of finite time period, which is referred to herein as the effective focal spot size of an x-ray exposure. The size of the static focal spot 127 significantly affects the heat loading capacity of the x-ray tube. With larger focal spots, greater heat loading is possible which allows a higher tube current mA to be safely provided. The size of the focal spot is determined by a combination of factors including the size and shape of the filament and the shape and bias voltage of the focusing cup. The angle of the target surface further defines a focal spot size along the so-called length direction.

The static focal spot 127 is therefore the focal spot as it appears from directly beneath the x-ray tube as seen by the breast, at near the chestwall position of patient.

Focal spot characteristics are defined by International Standard CEI IEC 60336. Focal spots are generally rectangular in shape, and are stated for two normal directions of evaluation referred to as the length and width direction. The length direction is generally parallel to a longitudinal axis of the x-ray system, and the width direction is generally perpendicular to the longitudinal axis. The longitudinal axis of an exemplary tomosynthesis system is shown in FIG. 1.

The size of the focal spot is a very important factor in a diagnostic x-ray tube because it affects the resolution of the radiography system; systems having smaller focal spots have better resolution. Thus it is often a design goal to minimize the static focal spot size. For example, mammography systems may be designed to provide a 0.3 mm focal spot for imaging (0.1 mm focal spot for high magnification images). According to one aspect of the invention it is realized that the movement of the x-ray source during image exposure effectively stretches the width of the static focal spot, resulting in an effective focal spot which is much wider than the static focal spot and which decreases image sharpness. The size of the effective focal spot is therefore determined by the size of the static focal spot and the motion of the static focal spot during exposure. The effective focal spot is therefore the accumulation of the static focal spot over time, and may also be referred to as the dynamic focal spot.

For example, during an exemplary tomosynthesis image scan, an x-ray tube may move from a position of −7.5° to a position of +7.5°. During the tube movement, a total of 15 exposures are performed, each having duration between 30-60 ms. During each exposure period, the x-ray tube continues to move along its path, thereby effectively 'stretching' the width of the static focal spot during the exposure to provide an effective focal spot of increased size.

Figure 2:
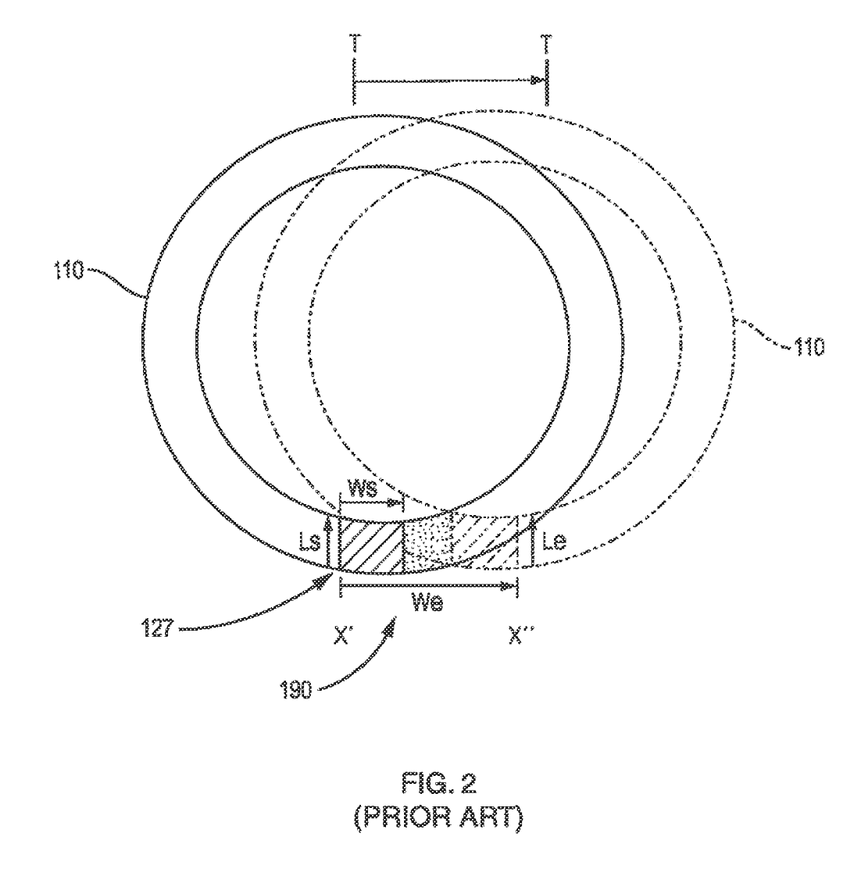
FIG. 2 is a cross section view of an x-ray tube provided to illustrate an effective focal spot of a prior art tomosynthesis system.

FIG. 2 is a cross section of x-ray tube 110 of FIG. 1 and illustrates the movement of x-ray tube 110 during one of the described tomosynthesis exposure periods. The static focal spot 127 of the x-ray tube is defined by a width Ws and length Ls and indicated by dashed box 127. At T=Exposure start, the x-ray tube is at a position X'. During the exposure period, the tube moves to a position X". The time-averaged effective focal spot 190 is defined by a width We and a length Le. Although the length of the effective focal spot corresponds to the length of the static focal spot, the width has increased. For example, in an exemplary tomosynthesis system with a static focal spot width of 0.3 mm, the effective focal spot width may increase to 1.5 mm during an exposure because the x-ray tube has moved 1.2 mm during the exposure period.

Figure 3A:
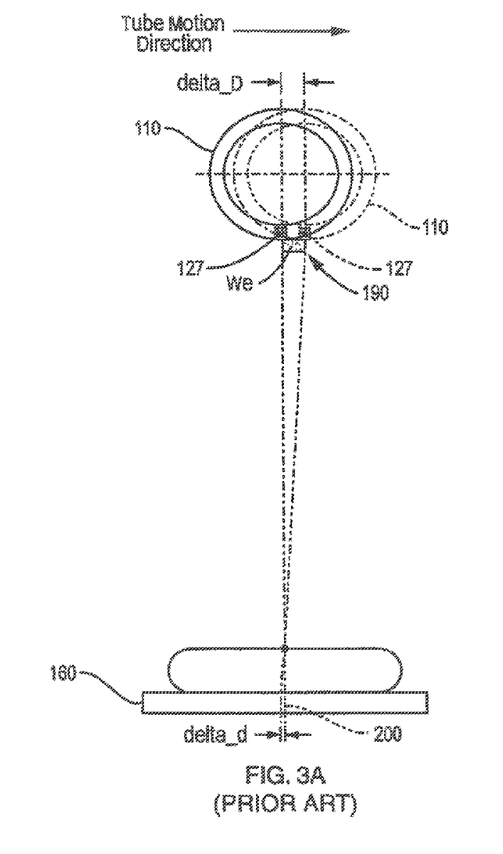
FIGS. 3A and 3B are cross section views of an x-ray tube and breast compression plate, and are used to illustrate motions of an static focal spot of an x-ray tube of the prior art and according to the present invention.
Figure 3B:
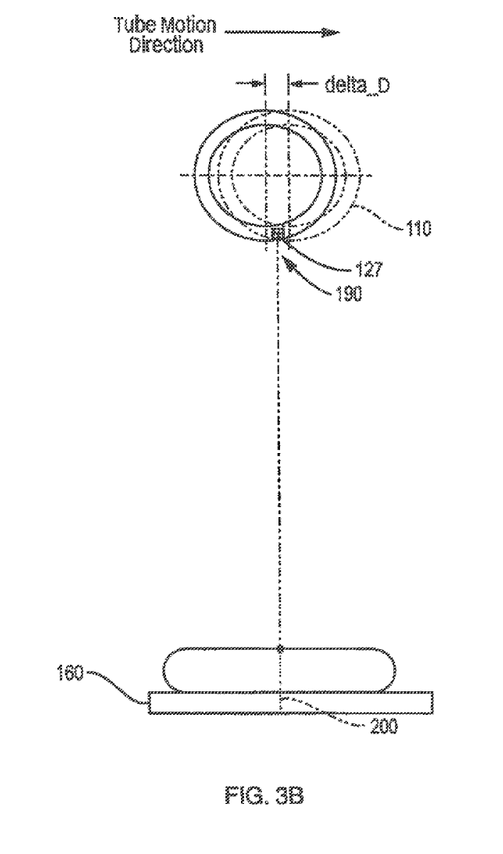

FIGS. 3A-3B also illustrate the motion of the x-ray source 110 over an exposure period, and further highlight the effect of the increased effective focal spot width on the image detector plane. As shown in FIG. 3A, the result of the increase in focal spot width can be seen in the imaging plane 160, where the delta in positions X' to X" (delta_D) translates into a shift of the focus spot during exposure by the amount represented as shaded element 200 (delta_d) so that a point object on the breast surface will be elongated to a size of delta_d.

The present invention recognizes that there is a direct relationship between the x-ray exposure time and the increase in size of the focal spot for tomosynthesis imaging. The relationship is problematic for at least the reason that denser breasts require longer exposure times for image acquisition, yet increased exposure time results in increased effective focal spot size and reduced image clarity because of focal spot blurring. The present invention further appreciates that the effective focal spot size is a function of the static focal spot size and the exposure period. The exposure period cannot always be shortened sufficiently so as to mitigate the effect of tube motion and minimize the effective focal spot size, because the tube current cannot be increased arbitrarily. Several approaches may be taken to reduce the effective focal spot size.

According to a first approach shown in FIG. 3B, the static focal spot is moved in a direction opposite to and generally synchronized with the directional movement of the x-ray source during the exposure period. In essence the movement of the static focal spot compensates for the movement of the x-ray tube, so that the effective focal spot appears to be fixed in space, relative to one of the breast and/or detector, in one position during the entire duration of the exposure. With such an arrangement image blurring may be reduced.

According to a second approach, the size of the static focal spot is increased. This allows higher x-ray tube current and thereby allows the exposure time to be decreased. Such an arrangement reduces the width of the effective focal spot while increasing the speed of a tomosynthesis scan and enabling full utilization of the x-ray tube capacity.

A third approach combines the above two approaches, using a relatively larger focal point in combination with a shorter exposure period, and moving the larger focal point during the exposure period.

An x-ray tube designed using any of the above approaches may be adapted to support both 2D and 3D imaging for systems that provide a combination of mammography and tomosynthesis imaging capability in a single system. For a 2D acquisition, the x-ray tube may provide smaller sized focal spots to provide standard mammograms or magnified images. In a 3D mode, the static focal spot size, position, or both may be controlled during imaging or in response to breast density to obtain images with increased clarity.

The above described approaches are described in detail below. However it is important to distinguish these approaches from flying focal spot techniques that have historically been used in computed tomography.

For example, U.S. Pat. No. 6,256,369 describes a system whereby a focal spot is made to oscillate in the longitudinal direction to improve scan throughput. In a preferred embodiment, the focal spot moves along a predefined path including a set of multiple positions displaced from one another in a longitudinal direction at each successive rotation angle. In effect the tube provides first and second fan beam planes. By alternating the focal spot between two longitudinal positions, the data are effectively sampled in two different z positions using two different fan beams, thereby doubling the throughput rate of the scanner.

U.S. Pat. No. 6,292,538 also describes an x-ray tube with flying focus. The flying focus technique of the '538 patent skips the focal point between two positions at high speed, effectively displacing images by a half pixel, in an attempt to improve resolution during CT scans.

In contrast, the present invention does not move the focal spot to different discrete positions to obtain multiple images during an exposure; rather, the object is to keep the effective focal spot in a fixed position in space, relative to either or both of the breast and/or detector, during the duration of the exposure through a slow controlled continuous movement of the focal point to enhance clarity in a single image.

The static focal spot is moved in a direction opposing the direction of the movement of the x-ray tube through space. As a result of the contrary movements of the x-ray tube and the static focal spot of the tube, the resulting effective focal spot maintains a fixed position relative to the breast and/or detector during each tomosynthesis exposure, minimizing the effective focal spot size and increasing image clarity.

Figure 4A:
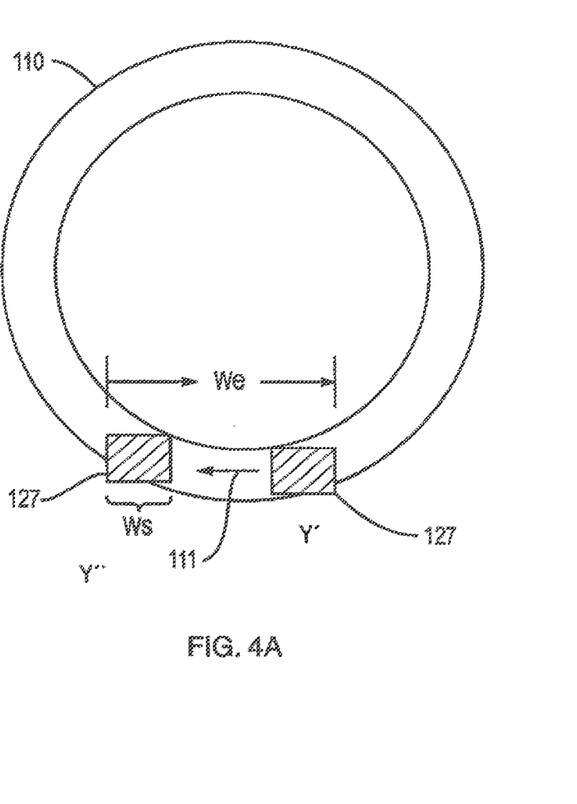
FIGS. 4A and 4B are cross section views of an X-ray tube provided to illustrate the motion of the static focal spot and resulting effective focal spot provided by an x-ray tube of the present invention.

FIG. 4A illustrates the movement of the static focal spot within an x-ray tube 110 during an exposure. In this figure the motion of the x-ray tube is not shown for clarity purposes although the tube is moved from left to right during the exposure period of this example. At the start of the exposure, the static focal spot is in position Y'. During the exposure, the static focal spot is moved at a rate of speed that matches or is otherwise related to the speed of the x-ray tube, in a direction opposed to the directional movement of the x-ray tube and indicated by arrow 111, until the static focal spot is in position Y''.

Figure 4B:
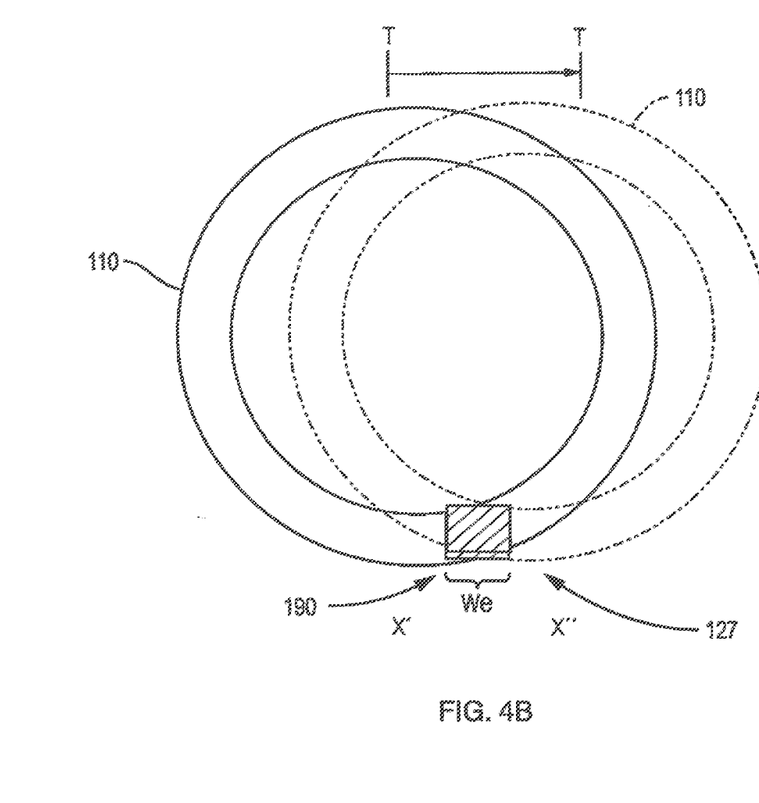

FIG. 4B illustrates the position of the static focal spot 127 during a tomosynthesis exposure when the static focal spot is moved in a manner shown in FIG. 4A. It can be seen that as the x-ray tube 110 is moved from position X' to position X'', the resulting effective focal spot 190 remains in a fixed or relatively fixed size and position relative to the detector 160 or imaged object; thus, although the x-ray tube is moving, the effective focal spot 190 appears to remain relatively fixed and minimally sized. As a result, there is no shift of focus at the detector, and the clarity of the tomosynthesis image is increased. Referring back to FIG. 3B, it can be seen that a point image on the breast generated as a result of the motion controlled focal spot will not experience the severe blurring effect of the prior art.

Thus a method for increasing x-ray image clarity in the presence of a moving x-ray source has been shown and described. Although the above description describes contrary movement of the x-ray tube and static focal spot in a single plane, it should be appreciated that the concepts of the present invention may be adapted to facilitate contrary movement of the focal spot from the x-ray tube in any dimension. In addition, the present invention is not limited to embodiments whereby the x-ray tube and focal spot are moved at the same speed, or over the same distance; it can be appreciated that the benefit of image clarity can be realized through any opposed motion of the static focal spot relative to the x-ray tube which minimizes the accumulation of the focal spot during x-ray exposure; thus the present invention is not limited to a particular range or directional speed for focal spot movement.

Figure 5A:
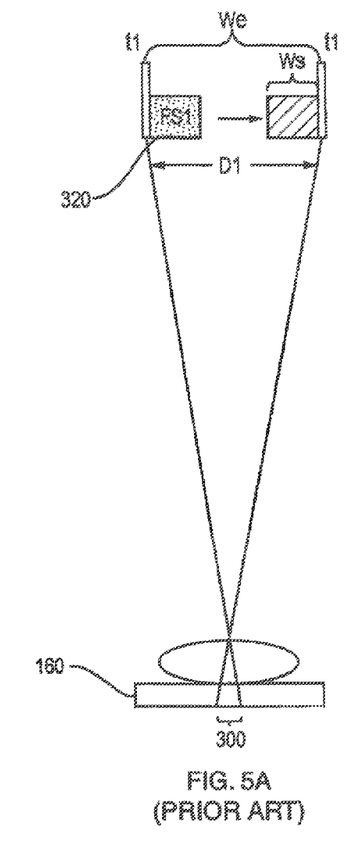
FIGS. 5A and 5B are also cross section views of an x-ray tube and breast compression plate, and are used to illustrate reduced image blurring that can be achieved by increasing an static focal spot while decreasing the exposure time for an x-ray image.
Figure 5B:
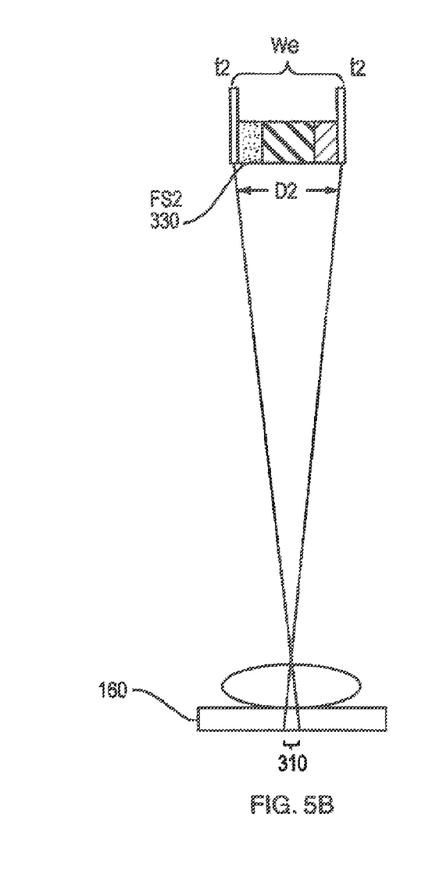

As described above, a second approach for reducing the effective focal spot size involves increasing the size of the static focal spot, but reducing the exposure period. For example, FIG. 5A is similar to FIG. 3A, where a relatively small static focal spot 320 is provided. To obtain the desired exposure for the image, the x-ray tube must be activated for duration D1, causing a blur effect 300 at the detector plane 160. As shown in FIG. 5B, if a relatively larger static focal spot 330 is provided, the total exposure time D2 may be reduced, resulting in a concomitant reduction in image blur 310. An advantage of providing a larger focal spot is that it permits full utilization of the x-ray tube generator. For example, current tomosynthesis x-ray tubes use a 200 mA generator but the generator does not always operate at the 200 mA because the desired, smaller static focal spot (for image clarity) allows only 160 mA at 28 kV. The present invention recognizes that the focal spot of a tomosynthesis image may be increased without sacrificing image clarity because the effect of an increased focal spot size is offset by the reduction in exposure time, so that a 'resulting' effective focal spot is smaller than previously obtained effective focal spots in the prior art.

The second approach may also have advantages for systems where the effective focal spot is larger than 1 cm due to physical constraints of focal spot movement. In such embodiments, enlarging the focal spot and reducing the exposure may yield the smallest focal spot for imaging.

A variety of techniques may be used to enlarge the focal spot size. The techniques include, but are not limited to: de-focusing the focus cup to allow larger focal spot sizes in the length or the width or both directions, incorporating additional electrodes to allow focal spot size change in one or both directions and incorporating a third filament or combination of the several filaments. In addition, sophisticated electron or x-ray optics techniques may be applied to enlarge focal spot sizes.

Accordingly, two methods for increasing x-ray image clarity in the presence of a moving x-ray source has been shown and described, wherein the first method involves moving the focal spot, and a second method involves increasing the size of the focal spot. It should be appreciated that either method may be used alone or in combination; for example, it is realized that providing an x-ray tube with a larger, moveable effective focal spot will result in a system that fully utilizes the x-ray tube generator, provides a high quality image and, due to the decrease in exposure time, may scan the patient more quickly.

In some embodiments it may be desirable to enable either automatic or manual selection of the use of either method, or the combination thereof. Either method may be realized by a modification to existing x-ray tube, for example by providing the ability to move the target, adjust the focus cup of the cathode, utilize different filaments or otherwise focus the x-ray photons.

Figure 6:
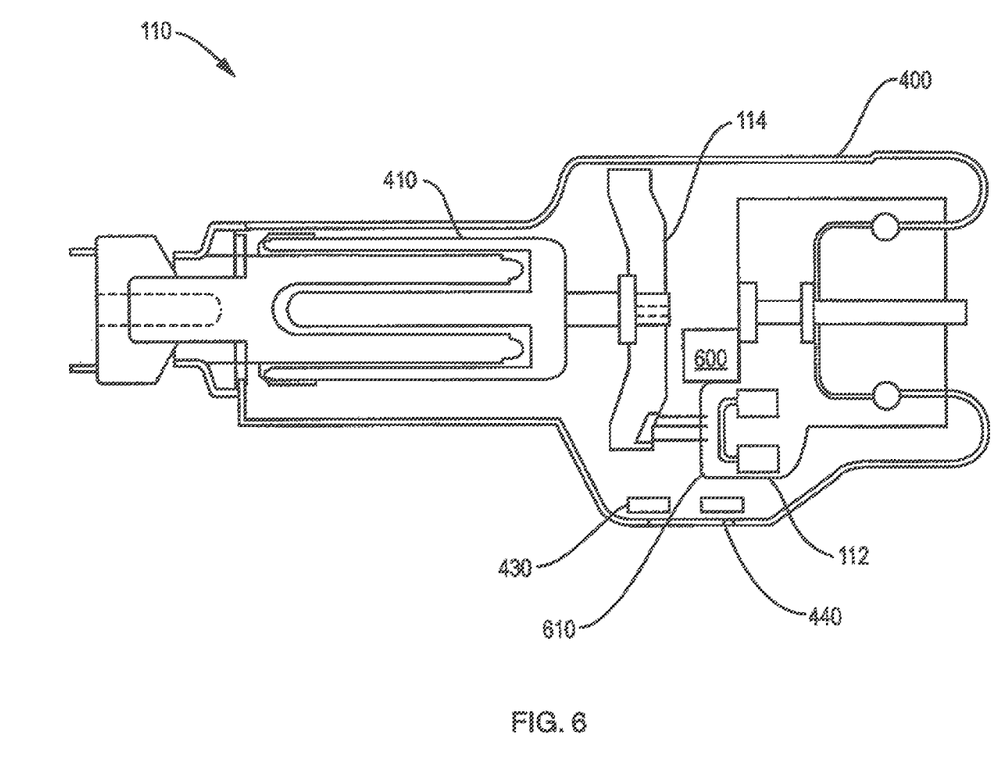
FIG. 6 is a diagram of an exemplary x-ray tube of the present invention.

For example, FIG. 6 illustrates an x-ray tube 110 of the present invention, which includes a vacuum tube 400 which encases an anode 114, a cathode 112 and an anode rotor 410. According to one aspect of the invention, the x-ray tube further includes a focal spot position controller 600. The focal spot controller may be coupled to the cathode 112 to deflect the electron trajectory in the 'width' direction. In its simplest form, the controller comprises two parallel metal plates located next to the focusing cup, with a bias voltage applied across the plates that can shift electron motion direction, and therefore the target location on the anode. The shift of the focal spot is therefore controlled via an application of a bias voltage across the plates. In several embodiments, the bias voltage can be dynamically or statically configured prior to x-ray exposure.

Figure 8A:
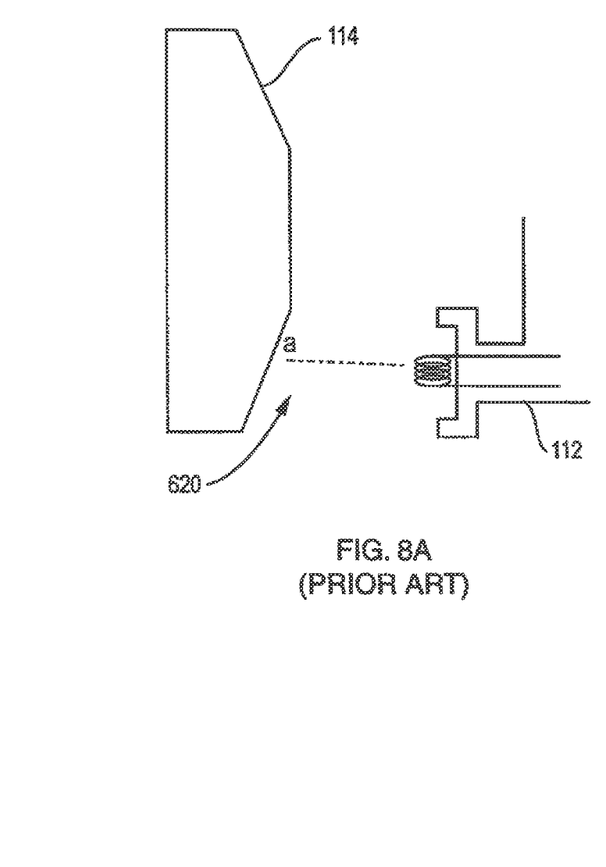
FIGS. 8A and 8B include diagrams of a target anode and an exemplary motion control element for controlling a movement of a focal spot on the anode.
Figure 8B:
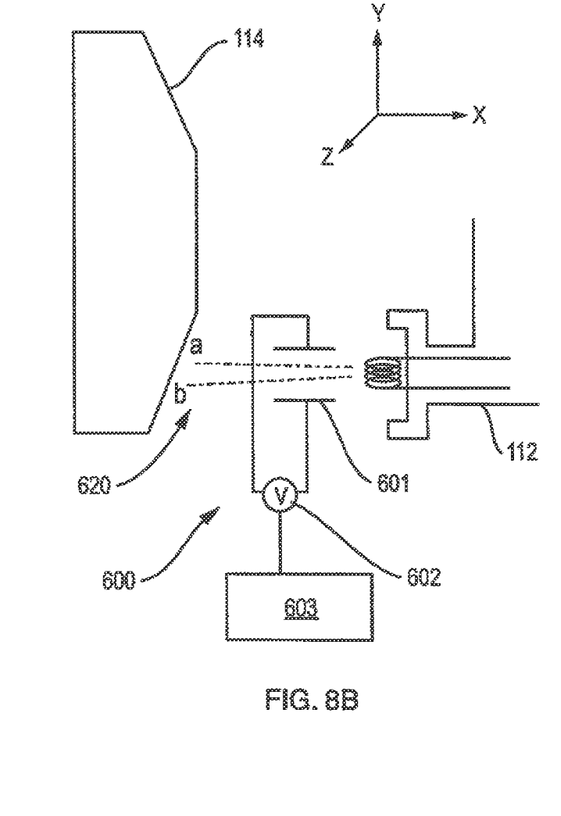

Referring briefly to FIGS. 8A and 8B, an exemplary mechanism for controlling the movement of a focal spot will now be described. In prior art, electrons emitted from the filament and cathode 112 travel along path 620 and hit the anode 114 at location a. This location a is the location of the focal spot.

In one embodiment of the present invention, motion control unit 600 is added. The motion control unit includes metal plates 601 and a voltage source 602 controlled by controller 603. Varying the voltage of the plates 601 varies the path of travel of the electrons to the target; for example, an electron will travel along one of the paths 620 and hit the anode 114 at different locations a and b depending upon the voltage applied to 601, where locations a and b represent different focal spot locations on the anode 114.

In FIG. 8B, the plates are shown aligned along a Y axis, and modifying the voltage of the plates changes the path of the electron along the Y axis. In the present invention, however, it is desirable to alter the path of the electron in the Z plane (normal to the page), and in such an embodiment, the motion controller would include plates aligned along the Z axis. Suffice it to say that the plates 601 can be in different geometric locations than shown in the figure, and there can be more than 1 set of plates. The number and arrangement of the plates, as well as the selection of voltage to be applied across the plates, be determined by the desired locations of the focal spots. Controller 603 will change the voltage over time to create the desired effective focal spot distribution, synchronized in an appropriate way with the tube motion and image receptor acquisition sequences.

In alternate embodiments, the focal spot controller controls a tilt of the anode to change the angle at which the electron stream from the cathode hits the anode target. In another embodiment, the controller moves the cathode focus cup so that the electrons hit the anode at a different target location or electronically deflects electron trajectory by applying a bias voltage applied orthogonally to the trajectory. Modifying the angle of electron engagement with the anode is one technique that can be used to control the static focal spot size, although any method that modifies the angle by which the electron stream engages the anode may be substituted herein as an equivalent. For example it is envisioned that similar results may be achieve through movement of the cathode filament or by other means.

Changing the relative angle between the anode and the cathode, and hence the angular direction at which electrons hit the target, may also accomplish the task of moving the position of the focal spot during a tomosynthesis exposure.

There are a variety of other methods that may be used to move the x-ray focal spot. In one embodiment, the focal spot may be moved using an x-ray lens within the tube or by adjusting the size and/or location of the tube port 120. The shifting of the electron beam focal spot may be accomplished by electronically steering the electron beam to a different spot on the x-ray target, electronically shifting the target, or by using an X-ray tube with one or more electron beam sources and distributed focal spots on one or more x-ray targets.

For example, to shift the X-ray beam focal spot, a first electron beam aimed at a first spot on the x-ray target could be turned off and a second electron beam aimed at a different second spot on the first or second x-ray target turned on. Since the electron beam strikes a different spot on the x-ray target, the x-ray beam will be emitted from a different spot on the target, thus shifting the position of the x-ray beam focal spot.

Alternatively, a fiber optic x-ray lens may also be used to shift the x-ray beam focal spot, by passing the beam through different fiberoptic strands of the bundle, with the strands directed towards slightly different directions. A shutter may be used to steer the beam into a particular strand or group of strands.

As mentioned above, it is also envisioned that the size of the focal spot may be changed to accommodate different modes of imaging. In an exemplary embodiment, an x-ray tube may be provided with three focal spot sizes: a small focal spot size: $0.1 \times 0.1$ mm$^2$, a large focal spot size: $0.3 \times 0.3$ mm$^2$, and an extra large focal spot size: $0.5 \times 0.5$ mm$^2$ or $0.6 \times 0.3$ mm$^2$ (Width×Length). The small focal spot and large focal spot may be used to support various 2D modes of imaging. The x-ray tube focal spot size may be configured to the extra large focal spot size in the 3D pulse mode when needed. With such an arrangement, an extra large focal spot size is provided on the anode track, allowing much higher tube current mA than the static 2D mode. The effective focal spot size associated with the extra large focal spot is expected to be $0.5 \times 0.5$ mm$^2$ or $0.6 \times 0.3$ mm$^2$.

Figure 9A:
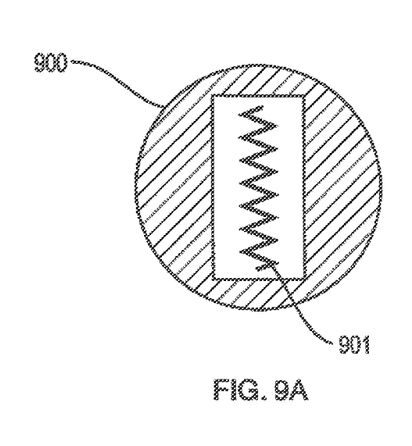
FIGS. 9A and 9B are diagrams illustrating the use of additional filaments in a focusing cup for increasing focal spot size.
Figure 9B:
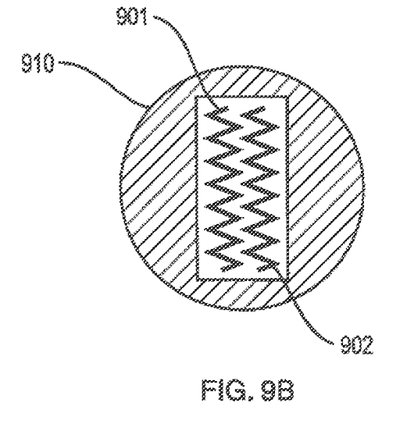

One method of changing the focal spot size involves adding filaments into the focusing cup. FIGS. 9A and 9B illustrates two embodiments of a focal spot cup 900 with different numbers of filaments 910 and 920. When one filament is lit, it provides an existing $0.3 \times 0.3$ mm focal spot. When both filaments are lit, the resulting filament emission capability is doubled, thus tube current is doubled, while focal spot size become $0.6 \times 0.3$ (width×length).

As mentioned above, the x-ray tube of the present invention may be provided in an imaging system which includes both 2D and 3D imaging capabilities. In such systems, the motion of the static focal spot and size of the static focal spot may differ between the two imaging modes. For example, the focal spot size may be increased for each tomosynthesis exposure, or during an entire scan, and reduced for modes, such as mammography, which require increased resolution and are not affected by x-ray source movement. The x-ray tubes are therefore configurable based on an imaging mode.

Figure 7:
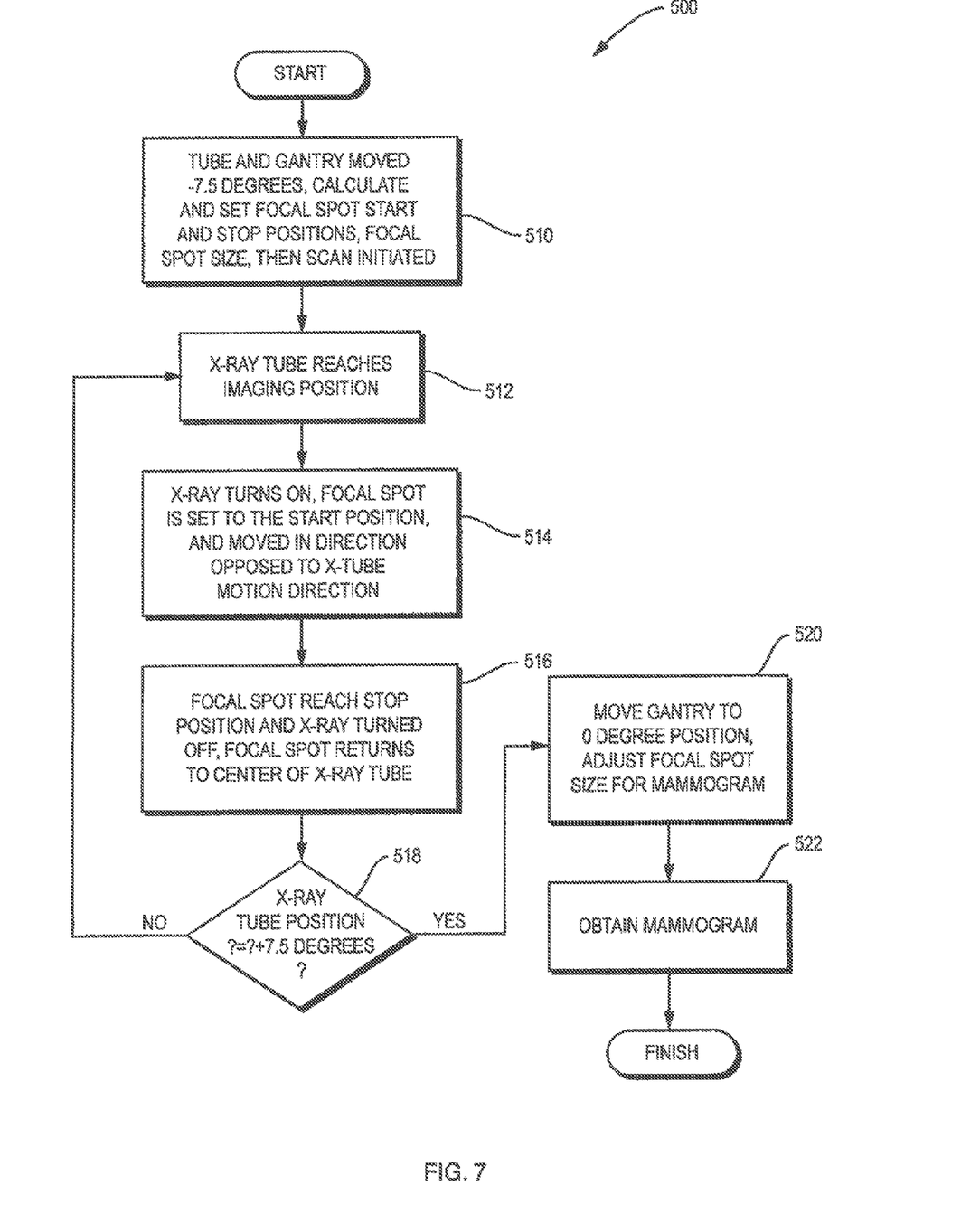
FIG. 7 is a flow diagram that is used to describe an exemplary process that may be followed during a tomosynthesis image scan using an x-ray tube having a moving focal spot of the present invention.

Referring now to FIG. 7, a process 500 of using an x-ray tube of the present invention in a system that supports 2D and 3D imaging will now be described. In the exemplary embodiment, the tomosynthesis system scans from −7.5 degrees to +7.5 degrees. A mammogram is taken following the tomosynthesis scan. At step 510 the gantry of a tomosynthesis machine is positioned at a −7.5 degree location and the tomosynthesis sweep is initiated. At step 512 the x-ray tube reaches an initial imaging position, and at step 514 the x-ray tube is activated. In one embodiment, each exposure takes less than 60 ms. During the exposure, the gantry continues to move towards the +7.5 degree position, and the x-ray tube focal spot motion controller sets the focal spot to a starting position on the anode which is pre-calculated based on the x-ray technique and gantry scan speed of the intended tomosynthesis scan, moves the static focal spot in the opposite direction (in this example, clockwise tomosynthesis scan).

At step 516, when the exposure is complete and focal spot at the same time reaches the pre-calculated stop position, the x-ray tube is turned off and the static focal spot is re-centered within the x-ray tube. At step 518 it is determined whether the end point of the clock wise scan has been reached (gantry at the +7.5 degree position). If not, the steps of 512-516 are repeated until all tomosynthesis projection images are obtained. At step 520 the gantry is returned to a zero degree position and the focal spot is optimized for mammography imaging. If the focal spot size had been increased for tomosynthesis imaging, it is reduced to the range which provides desired mammogram resolution. At step 522 the 2D image is obtained and the process is complete. It should be noted that the above text has described a system whereby the x-ray tube is turned 'on' or 'off.' However, it should be noted that the present invention is not limited to such a system. In fact, many systems have x-ray tubes that are continuously on during the scan, with image capture being controlled by capture of the x-rays at the detector at select 'exposure times' times during the scan. In such instances, it can be appreciated that the focal spot motion is synchronized to the exposure start and exposure end times, regardless of whether the x-ray tube is cycled on or off, or is continuously on.

Accordingly, a system, method and process of the present invention has been shown and described whereby tomosynthesis image clarity is improved by static or dynamic management of focal spot size and position during an x-ray exposure. It should be noted that although the description has centered on the use of a tomosynthesis system for breast imaging, the x-ray tubes of the present invention are not limited for use to any particular imaging modality. Rather it is envisioned that the x-ray tubes of the present invention may have utility in any system which obtains images while an x-ray source is in motion. For example, computed tomography (CT) systems experience focal spot blurring. The modified x-ray tube of the present invention may advantageously be used with CT systems to reduce the FS blur, making the Modulation Transfer Function (MTF) across field of view isotropic. In a breast CT system, one benefit of such an improvement would be that the MTF at the breast edge would be as good as that in the breast center in the horizontal plane. The above specific examples and embodiments are illustrative, and many variations can be introduced on these examples and embodiments without departing from the spirit of the disclosure or from the scope of the appended claims. For example, elements and/or features of different illustrative embodiments may be combined with each other and/or substituted for each other within the scope of this disclosure and appended claims.

Various embodiments of the invention include an x-ray tube arranged to move during an exposure period. The x-ray tube includes a cathode for providing an electron stream, an anode comprising a target for receiving the electron stream, the anode for generating a photon stream, a focusing cup which focuses the electron stream on the anode during the exposure period, a port for passing the photon stream out of the x-ray tube, wherein the cathode, anode and port together define an static focal spot of the x-ray tube, and a controller coupled to at least one of the anode, the cathode and focusing cup for modifying a characteristic of the static focal spot during the exposure period by performing at least one of modifying a static focal spot location or size in relation to a movement of the x-ray tube.

The x-ray tube may move in a first direction during the exposure period and the controller may move the static focal spot in a second direction, opposite to the first direction, during the exposure period such that an effective focal spot remains relatively fixed in space relative to the breast and/or detector during the exposure period to reduce image blur. The static focal spot size may be increased to reduce the exposure period and resulting image blur.

In accordance with another aspect of the invention, a method of acquiring an x-ray image using an x-ray tube that moves in a first direction during an exposure period includes the step of moving a focal spot of the x-ray tube in a second direction opposite to the first direction during the exposure period to reduce an effective focal spot size during the exposure period.

According to a further aspect of the invention, a method of acquiring an x-ray image by an imaging system capable of operating in two modes, the method including the step of varying a size of a focal spot of an x-ray tube in response to an operating mode of the imaging system. The method may include the step of varying the size of the focal spot increases the size of the focal spot in imaging modes wherein images are acquired using an x-ray tube which moves during an exposure period. In addition, the step of varying the size of the focal spot may decrease the size of the focal spot in imaging modes wherein images are acquired using an x-ray tube which remains in fixed position relative to the breast and/or detector during the exposure period.

The foregoing of preferred embodiments has been presented as an illustration of examples and is not intended to be exhaustive or to limit the claimed inventions to the specific examples. Those examples are intended to describe principles that persons skilled in the art may use to practice the claimed inventions, using variations and modifications of the disclosed examples that are suited to a particular environment. It is intended that the scope of the invention be defined by the appended claims and their equivalents.

We claim:

1. An x-ray imaging system for obtaining images of a patient's breast comprising:
    an x-ray tube comprising an x-ray source and a static focal spot when the x-ray tube is in operation, wherein a size of the static focal spot automatically varies in response to various selected operating modes of the system, wherein the various selected operating modes comprise at least a mammography operating mode and a tomosynthesis operating mode, and wherein the x-ray source is configured to move along an arc when in the tomosynthesis operating mode; and
    an x-ray detector positioned to receive x-rays from the x-ray source during an exposure period of the x-ray source,
    wherein the static focal spot for one of the selected operating modes is of larger size than the static focal spot for another selected operating mode and wherein a size of the static focal spot changes in response to breast density of the patient's breast.

2. The x-ray imaging system of claim 1, wherein the static focal spot is larger in the tomosynthesis operating than the static focal spot in the mammography operating mode.

3. The x-ray imaging system of claim 2, wherein an exposure period of the x-ray source in the tomosynthesis operating mode is less than an exposure period of the x-ray source in the mammography operating mode.

4. The x-ray imaging system of claim 3, wherein, during an exposure in the tomosynthesis operating mode, the static focal spot is moved in a direction opposite to and generally synchronized with a directional movement of the x-ray source.

5. The x-ray imaging system of claim 1, wherein a size of the static focal spot is controlled by a controller.

6. The x-ray imaging system of claim 2, wherein the size of the static focal spot is larger in the tomosynthesis operating mode due to adjustments of a focus cup that is attached to a cathode of the x-ray tube.

7. The x-ray imaging system of claim 6, wherein the size of the static focal spot is larger in the tomosynthesis operating mode due to two or more different filaments in the focus cup in which two of the two or more different filaments are lit.

8. The x-ray imaging system of claim 2, wherein the size of the static focal spot is larger during each exposure in the tomosynthesis operating mode than the size of the static focal spot during an exposure in the mammography operating mode.

9. The x-ray imaging system of claim 2, wherein the size of the static focal spot is larger for an entire scan of the x-ray source in the tomosynthesis operating mode.

10. A mammography and tomosynthesis x-ray imaging system for obtaining images of a patient's breast comprising:
    an x-ray tube comprising an x-ray source and a static focal spot when the x-ray tube is in operation, wherein the static focal spot is configured to be selectively altered automatically during an exposure of a tomosynthesis operating mode of the x-ray imaging system and wherein the x-ray source is configured to move along an arc when in the tomosynthesis operating mode; and
    an x-ray detector positioned to receive x-rays from the x-ray source during an exposure period of the x-ray source,
    wherein the static focal spot is selectively altered automatically between a plurality of modes, a first mode comprising enlarging a size of the static focal spot during the exposure and a second mode comprising moving the static focal spot in a direction opposite to a directional movement of the x-ray source during the exposure,
    wherein the static focal spot selectively alters in response to breast density of the patient's breast.

11. The mammography and tomosynthesis x-ray imaging system of claim 10, wherein a third mode of selectively altering the static focal spot comprises enlarging a size of the static focal spot and moving the static focal spot in a direction opposite to a directional movement of the x-ray source during the exposure.

12. The mammography and tomosynthesis x-ray imaging system of claim 10, wherein an exposure period of the x-ray source in the tomosynthesis operating mode is less than an exposure period of the x-ray source in a mammography operating mode.

13. The mammography and tomosynthesis x-ray imaging system of claim 10, wherein the static focal spot is controlled by a controller to selectively alter the static focal spot.

14. The mammography and tomosynthesis x-ray imaging system of claim 10, wherein the the static focal spot is selectively altered in the tomosynthesis operating mode due to adjustments of a focus cup that is attached to a cathode of the x-ray tube.

15. The mammography and tomosynthesis x-ray imaging system of claim 10, wherein the size of the static focal spot is larger during each exposure in the tomosynthesis operating mode than the size of the static focal spot during an exposure in a mammography operating mode.

16. The mammography and tomosynthesis x-ray imaging system of claim 10, wherein the static focal spot is automatically altered between the plurality of modes.

17. A mammography and tomosynthesis x-ray imaging system for obtaining images of a patient's breast comprising:
    an x-ray tube comprising an x-ray source and a static focal spot when the x-ray tube is in operation, wherein the static focal spot is configured to be selectively altered during an exposure of a tomosynthesis operating mode of the x-ray imaging system and wherein the x-ray source is configured to move along an arc when in the tomosynthesis operating mode; and
    an x-ray detector positioned to receive x-rays from the x-ray source during an exposure period of the x-ray source,
    wherein the static focal spot is selectively and manually altered between a plurality of modes, a first mode comprising enlarging a size of the static focal spot during the exposure and a second mode comprising moving the static focal spot in a direction opposite to a directional movement of the x-ray source during the exposure.

* * * * *